(12) United States Patent
Graves et al.

(10) Patent No.: US 8,830,451 B1
(45) Date of Patent: Sep. 9, 2014

(54) MULTINODE ACOUSTIC FOCUSING FOR PARALLEL FLOW CYTOMETRY ANALYSIS APPLICATIONS

(75) Inventors: Steven Wayde Graves, Santa Fe, NM (US); Robert W. Applegate, Jr., Santa Fe, NM (US); Gabriel Lopez, Durham, NC (US); Menake Eranda Piyasena, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 147 days.

(21) Appl. No.: 13/103,756

(22) Filed: May 9, 2011

Related U.S. Application Data

(60) Provisional application No. 61/395,190, filed on May 7, 2010.

(51) Int. Cl.
| | | |
|---|---|---|
| *G01N 21/00* | (2006.01) | |
| *G01N 15/02* | (2006.01) | |
| *G01N 15/14* | (2006.01) | |

(52) U.S. Cl.
CPC ........ *G01N 15/1459* (2013.01); *G01N 15/0205* (2013.01)
USPC .......................................................... 356/73

(58) Field of Classification Search
CPC ................................................. G01N 15/0205
USPC .................... 356/335, 338, 244, 246
See application file for complete search history.

(56) References Cited

U.S. PATENT DOCUMENTS

| | | | | |
|---|---|---|---|---|
| 3,826,364 A | * | 7/1974 | Bonner et al. ................. | 209/3.1 |
| 4,573,796 A | * | 3/1986 | Martin et al. ................. | 356/318 |
| 5,225,089 A | * | 7/1993 | Benes et al. ............. | 210/748.05 |
| 5,682,038 A | * | 10/1997 | Hoffman .................... | 250/458.1 |
| 6,273,262 B1 | * | 8/2001 | Yasuda et al. ..................... | 209/1 |
| 6,743,638 B1 | * | 6/2004 | Tsilosani et al. .............. | 436/518 |
| 7,217,393 B2 | | 5/2007 | Witty et al. | |
| 7,340,957 B2 | | 3/2008 | Kaduchak et al. | |
| 7,709,821 B2 | | 5/2010 | Casstevens et al. | |
| 2003/0096430 A1 | * | 5/2003 | Holl et al. ..................... | 436/177 |
| 2004/0184960 A1 | | 9/2004 | Tanaami | |
| 2006/0037915 A1 | * | 2/2006 | Strand et al. ................... | 210/748 |
| 2008/0245745 A1 | * | 10/2008 | Ward et al. ................... | 210/748 |
| 2009/0158823 A1 | * | 6/2009 | Kaduchak et al. ........... | 73/61.75 |

FOREIGN PATENT DOCUMENTS

| | | |
|---|---|---|
| KR | 1020090034245 | 4/2009 |
| WO | 2011017681 A2 | 2/2011 |

OTHER PUBLICATIONS

Surendra K. Ravula, "A microfluidic system combining acoustic and dielectrophoretic particle preconcentration and focusing" Oct. 23, 2007.*

Surendra K. Ravula "A microfluidic system combining acoustic and dielectrophoretic particle preconcentration and focusing" Oct. 23, 2007.*

(Continued)

*Primary Examiner* — Kara E. Geisel
*Assistant Examiner* — Maurice Smith
(74) *Attorney, Agent, or Firm* — Gonzales Patent Services; Ellen M. Gonzales

(57) ABSTRACT

An analytical device such as a flow cytometer is provided in which a fluid sample flowing through a channel is focused into multiple, parallel particle streams by an acoustic wave field extending across the channel. Each stream is then presented to an individual detector to allow for simultaneous interrogation of the multiple streams and thus, high-throughput analysis of the fluid sample.

18 Claims, 8 Drawing Sheets

(56) References Cited

OTHER PUBLICATIONS

Gregory Goddard. "Ultrasonic Particle-Concentration for Sheathless Focusing of Particles for Analysis in a Flow Cytometer", Oct. 11, 2005.*

Chretien, Marie Françoise, et al. "Cytomorphometric analysis of vaginal cells during normal cycle, under oral contraceptive therapy or in-vitro fertilization stimulation protocol." Human Reproduction 13.10 (1998): 2767-2771.

Goddard, Gregory, et al. "Ultrasonic particle—concentration for sheathless focusing of particles for analysis in a flow cytometer." Cytometry Part A 69.2 (2006): 66-74.

Stephens RWB, Bate AE, Acoustics and vibrational physics: pp. 138-141, Edward Arnold London; 1966.

* cited by examiner

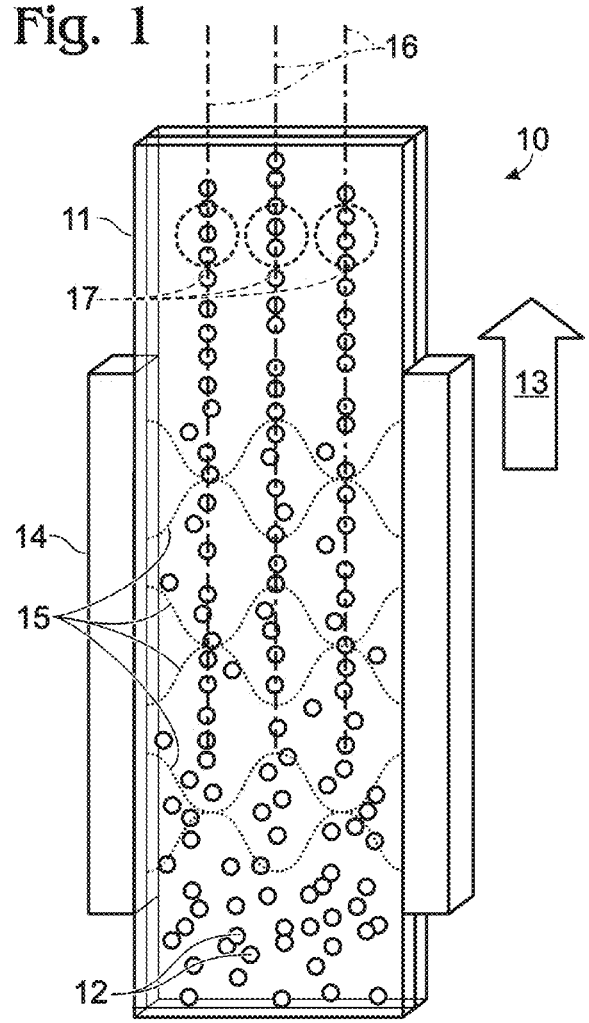
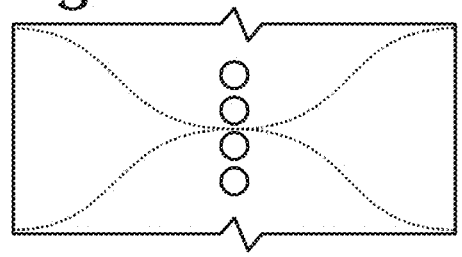
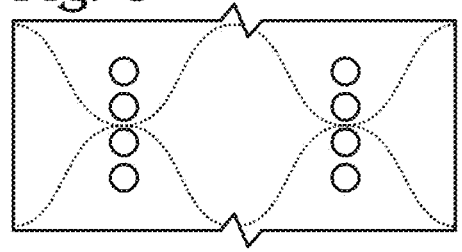
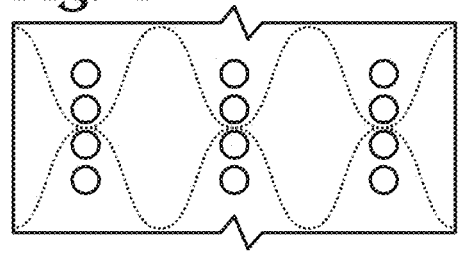

MULTINODE ACOUSTIC FOCUSING FOR PARALLEL FLOW CYTOMETRY ANALYSIS APPLICATIONS

CROSS-REFERENCE TO RELATED APPLICATIONS

The following application claims benefit of U.S. Provisional Application No. 61/395,190, filed May 7, 2010, which is hereby incorporated by reference in its entirety.

BACKGROUND

Flow cytometry is a powerful analytical technique used to measure many properties and investigate many parameters of cells, engineered microspheres, microscopic organisms, and particles in solution for applications that range from biomedical diagnostics to monitoring of environmental states.[1-4] In conventional flow cytometry, a suspension to be analyzed is focused into a single, fine stream using hydrodynamic focusing by a high-pressure sheath fluid that constricts the sample. In combination with a tightly focused laser this precise positioning creates a small interrogation volume that is analyzed via high numerical aperture optics. The collected light is typically distributed via conventional optics to several photodetectors to provide multiple parameters of fluorescence and scatter for each cell or particle. Conventional flow cytometers can analyze cells at rates as high as 50,000 cells/sec[5] but for many applications that have clinical relevance such as the detection of circulating tumor cells (CTC) that are present in blood at levels as low as a 100 cells per milliliter of blood, the current analysis speed of conventional flow cytometers is inadequate.[6] Accurate and simple detection of CTCs in blood samples is becoming a highly sought after diagnostic for cancer detection and treatment monitoring applications.[7] Additional clinical applications, such as detection of fetal cells in maternal blood for prenatal diagnosis[8-10] and endothelial progenitor cells that have roles in cancer and cardiovascular disease,[11-13] which require analysis of billions of cells in regular basis, could also benefit from improved analysis rates.

While the need for high analysis rates to support rare event detection applications has been recognized, higher analysis rates are limited in conventional flow cytometry by several parameters that include: detector sensitivity, data acquisition electronics, system pressure, and coincidence rates of particles within the analysis point of the flow cytometer. Detector sensitivity limits the rate of analysis since increasing particle analysis rates typically results in shorter interrogation times, which has led to the use of highly sensitive and fast detectors such as photomultiplier tubes or avalanche photodiodes. Extremely short transit times also pose a challenge for data acquisition where digitization of signals from multiple detectors with 14-bit analog-to-digital converters (ADCs) running at nearly 100-MHz greatly increase the cost and complexity of the system. Additionally, as the linear velocity of the sample stream is proportional to the square root of the sample delivery pressure, conventional systems require greater than 1 MPa to drive samples at 10 m/s.[14] Thus, mechanical limitations of the flow cell as well as deleterious effects on cells can restrict the pressure being applied to the system. Finally, the maximum analysis rate is also determined by the stochastic nature of cellular arrival at the interrogation volume, which limits the concentrations of cells that can be used without causing an intolerable number of coincidences following the Poisson distribution of particle arrival times. Due to a combination of the above limitations, a conventional single stream flow cytometer is roughly limited to an analysis rate of 50,000 cells per second.[5]

To achieve higher analysis rates it has become necessary to explore the use of parallel analysis streams. For numerous reasons, the use of multiple independent channels (regardless of shape) with independent focusing elements would likely be unacceptably complex. Accordingly there is a need for mechanisms to produce multiple stream lines in a single channel. To a modest extent this approach has been successfully achieved via the use of four hydrodyamically focused simultaneous stream lines, which enables analysis and sorting at rates reported to be greater than 250,000 cells per second.[15] However, alternative approaches to particle focusing such as acoustic, inertial, and dielectrophoretic positioning have the advantage of concentrating particles to precise positions without the concurrent acceleration imparted by hydrodynamic focusing.[16-25] These approaches offer the potential to create many parallel streams with modest linear velocities, which might greatly simplify the creation of highly parallel flow cytometers with even higher analysis rates and greatly reduced system cost and complexity. Furthermore, these techniques do not require a sheath flow, thus fluid consumption and hazardous waste output is minimized.

While the concept of highly parallel flow streams has been explored in part through the use of highly parallel inertial focusing channels,[19] there may be distinct advantages to the use of acoustic focusing. Acoustic focusing employs an ultrasonic standing wave to position particles suspended in a fluid-filled cavity, via a time-averaged drift force that transports them to a nodal or anti-nodal position.[26] If particles are more compressible and less dense than the surrounding fluid then they are driven to the pressure antinodes of a standing wave, while if they are denser and less compressible than the surrounding fluid they are driven to the pressure nodes.[17]

Acoustic focusing cells in a variety of forms have been developed for a many applications.[27-33] In planar standing waves, particles are typically regularly spaced at half-wavelength intervals parallel to the direction of acoustic wave propagation.[16,19,34] However, the use of cylindrical transducing elements can drive standing waves with a two dimensional structure and an axially positioned focusing node in the center of the capillary, which is analogous to how a traditional hydrodynamic focusing flow cell functions.[35] As the optimal resonant frequency of all acoustic cells varies based on the viscosity, density, and temperature of the sample, this approach requires active control to maintain optimal focusing.[35,36]

BRIEF DESCRIPTION OF THE DRAWINGS

FIG. 1 is a schematic drawing of an acoustic flow cell according to an embodiment of the present disclosure.

FIG. 2 shows the formation of a single pressure node producing a single particle stream.

FIG. 3 shows the formation of two pressure nodes producing two distinct particle streams.

FIG. 4 shows the formation of three pressure nodes producing three distinct particle streams.

FIG. 6 is a long range photo showing 24 distinct streams produced at a 1.17 MHz.

FIG. 7 is a close-up of some of the streams of FIG. 6.

FIG. 8 is a long range photo showing 33 distinct streams produced at 1.54 MHz.

FIG. 9 is a close-up of some of the streams of FIG. 8.

FIG. 12 is the flow cytometric analysis of a first stream and yielded a CV of 5.2%.

FIG. 13 is the flow cytometric analysis of a second stream and yielded a CV of 6.3%.

FIG. 14 is the flow cytometric analysis of a third stream and yielded a CV of 7.6%.

DETAILED DESCRIPTION

Figure 5:
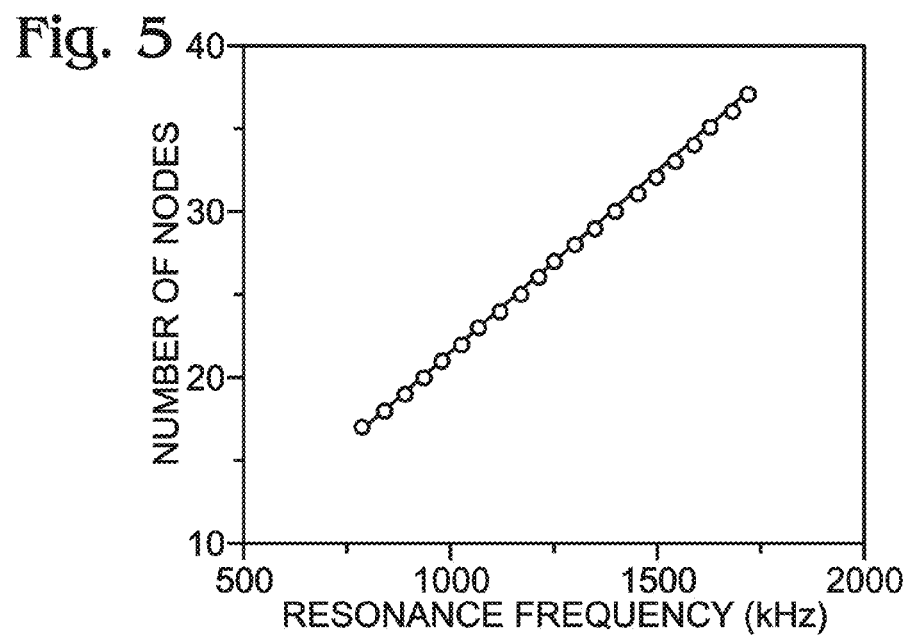
FIG. 5 is a graph showing the observed and theoretically expected number of focused streams of 10 μm particles generated at varying applied resonance frequencies (circles are observed streams while the line shows the expected number of streams.

According to various embodiments the present disclosure provides methods and apparatus for parallel flow cytometry using multi-node acoustic focusing. According to a specific embodiment, the present disclosure provides acoustic focusing flow cells for flow cytometry. According to another embodiment the present disclosure provides methods for high-throughput, parallel analysis of fluid samples by using multinode acoustic standing waves to focus particles and cells in the sample into multiple parallel streams. Furthermore, the presently described devices and methods can be used to focus of particles sized from as small as 1 μm to greater than 100 μm. Furthermore, it will be understood that the devices and methods described herein are applicable to less conventional applications such as the analysis of larger particles including, but not limited to, tumor microspheroids, one-bead-one compound particle libraries, and small multicellular organisms.

FIG. 1 is a schematic drawing of an acoustic flow cell according to an embodiment of the present disclosure. As shown, the acoustic flow cell 10 includes a capillary 11 through which a sample 12 can flow. The direction of the fluid flow is shown by arrow 13. According to various embodiments the capillary may be formed from glass, silicon, plastic or any other material through which the acoustic wave field may be directed. The capillary may be rectangular in shape. Alternatively, the capillary may be any suitable shape including V-shaped, square, or any other desired shape. An acoustic wave generator 14 produces an acoustic wave field 15 which extends across the width of capillary 11. Those of skill in the art will recognize that any suitable mechanism for producing an acoustic wave could be used including, for example, a piezoelectric element which converts electrical pulses into mechanical vibrations and vice versa. In some embodiments it may be desirable to also include a second piezoelectric element on the opposing side of the first element to pick up feedback signals. The acoustic wave field focuses the particles in the sample to the various nodes of the wave field, producing multiple parallel particle streams 16 which then flow in parallel through the capillary towards and then through one or more analysis regions 17. Accordingly, in the present disclosure, the acoustic focusing technique is employed to produce a flowing system that enables simultaneous analysis of multiple streamlines of particles within the same flow cell.

It will be appreciated that the acoustic flow cell may utilize any suitable mechanism to drive fluid flow through the capillary including, but not limited to, gravity-driven mechanisms, electrical, mechanical, or chemical pumps, or the like.

The number of focused stream generated in a given capillary depends on the wavelength and the cross-sectional channel width. The corresponding channel width for a particular number of nodes and wavelength can be calculated from the equation below, where L is the width of the channel, n is the number of nodes and λ is the acoustic wavelength.

$$L = n\lambda/2 \tag{1}$$

For example when the half wavelength (λ/2) of the resonance frequency matches with width (L) of the capillary a single pressure node (n=1) is formed, as shown in FIG. 2. As the frequency is increased, the wavelength is shortened, the standing wave resonates at higher harmonics and thus results in increased numbers of nodes and antinodes, see FIGS. 3 and 4. Accordingly, by manipulating the wavelength of the acoustic wave field, the presently described flow cell can be designed to divide the particles in the fluid sample into any desired number of independent streamlines, limited only by the physical size constraints of the capillary.

Figure 6:
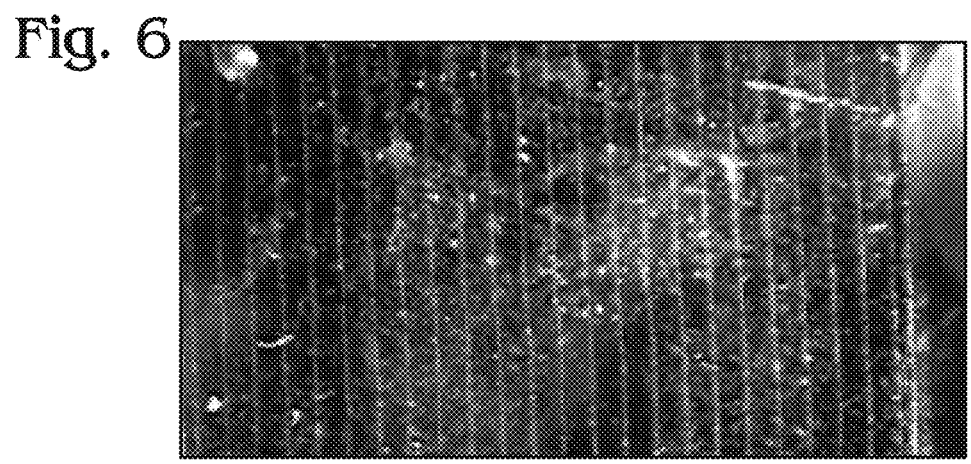
FIGS. 6-9 show the formation of highly parallel focused streams of 10 μm particles using a device as described herein with different resonance frequencies.
Figure 7:
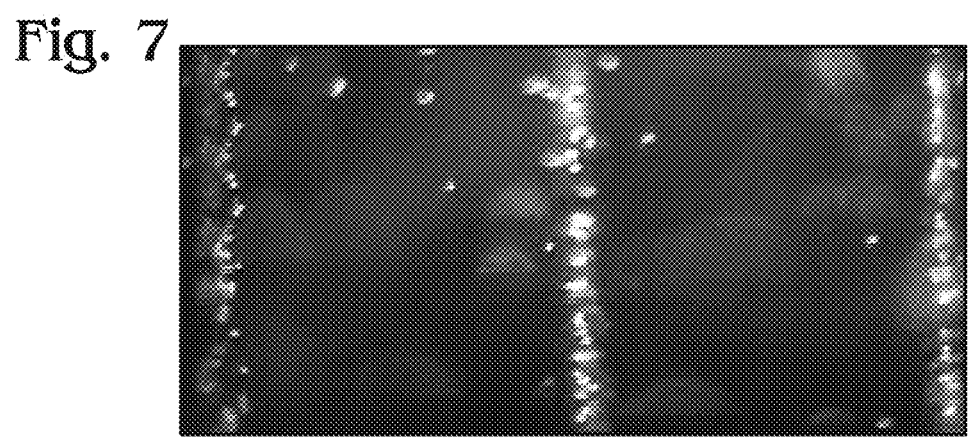
Figure 8:
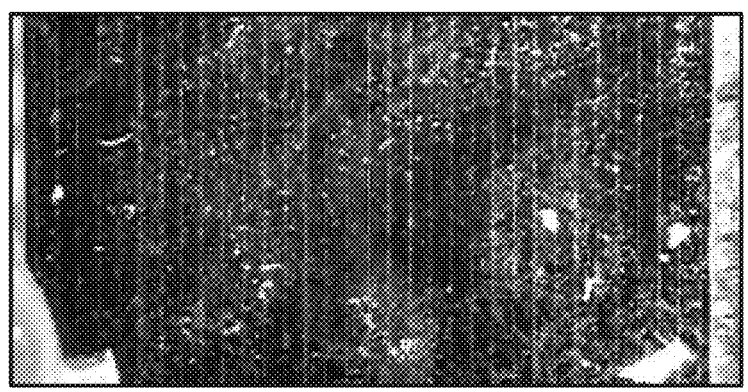
Figure 9:
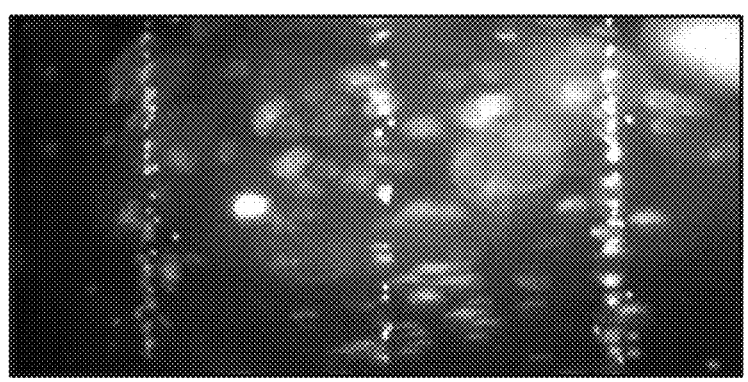

In the highly parallel acoustic focusing system the number of streams generated at a given frequency was identical to the theoretical, half wavelength value (FIG. 5), which is unique for this planar flow cell as compared to the capillary based flow cells which significantly deviate from predicted frequencies (see above). The theoretical values for number of focused streams (nodes) can be calculated by re-arranging the equation (1) to obtain the following expression, $$n = 2L\nu/C \tag{2}$$

Where ν and C are applied resonance frequency and the speed of sound in water at room temperature, respectively. We assumed the speed of sound in water as 1480 m/s. The predictable number of nodes generated by this flow cell enable us to easily create focused streamlines ranging from 17 to 37 streams across the flow cell and we show images of a subset of these frequencies that generate 24 and 33 streams of 10 μm silica particles at 1.17 and 1.54 MHz respectively (FIGS. 6 and 8). Captured images at close range (FIGS. 7 and 9)

indicate that focused streams are well resolved and have very good focusing without any sample cross-over.

Figure 10:
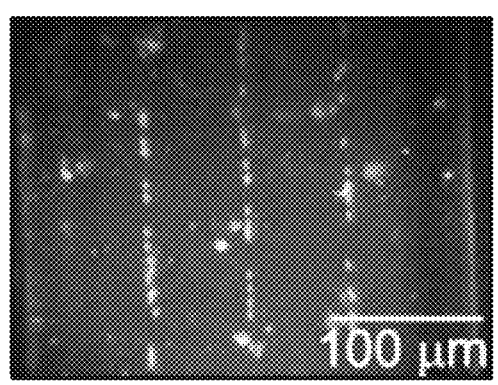
FIG. 10 is an optical micrograph showing the focusing of 10 μm particles into three distinct streams.
Figure 11:
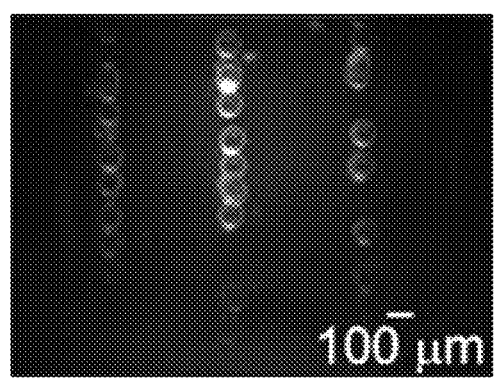
FIG. 11 is an optical micrograph showing the focusing of 107 μm particles into three distinct streams.

Furthermore, the presently described flow cell is capable of focusing a wide range of particle sizes. For example, using the flow cell described herein, we have demonstrated effective focusing of particle sizes ranging from 10 μm (FIG. 10) to larger than 100 μm (FIG. 11). As acoustic focusing results from a time averaged drift force that is proportional to particle diameter,[38,39] we expect that parallel analysis flow cells of this type would be effective for particles as small as a micron and thus effective for almost all types of cells.[40,41]

Figure 12:
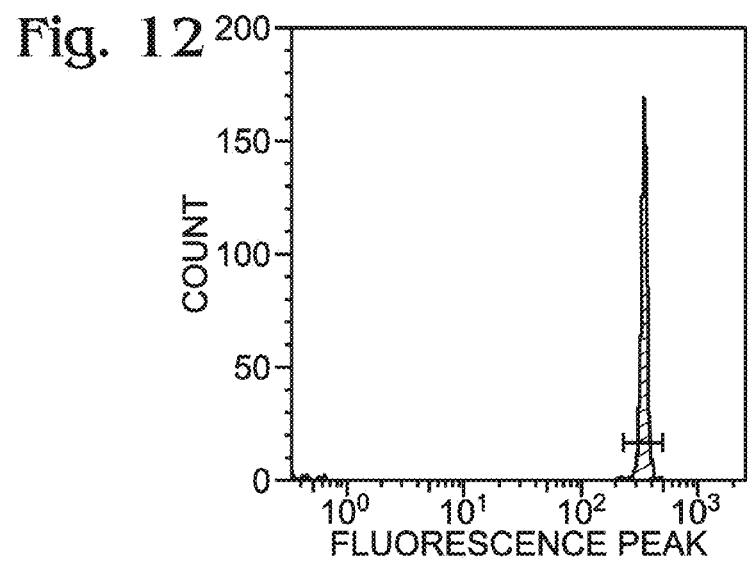
FIGS. 12-14 show flow cytometric analysis of acoustic focusing of three distinct streamlines of 107 μm red fluorescent polystyrene particles flowing at 1.6 mL/min and analyzed individually.
Figure 13:
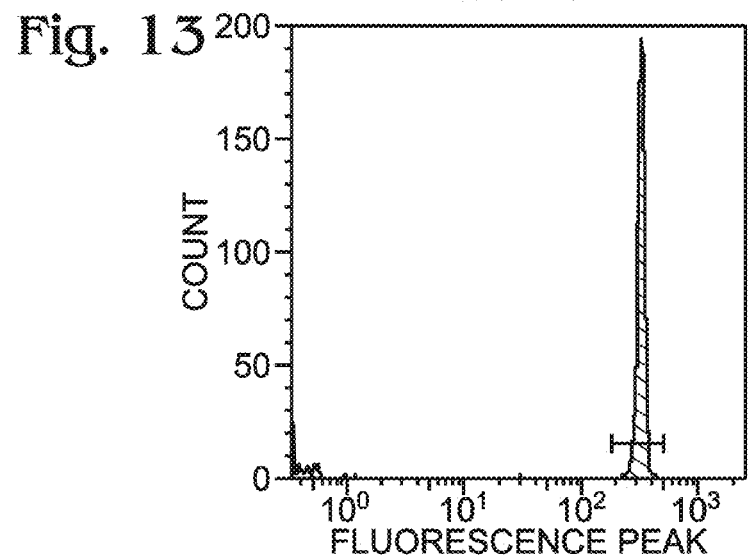
Figure 14:
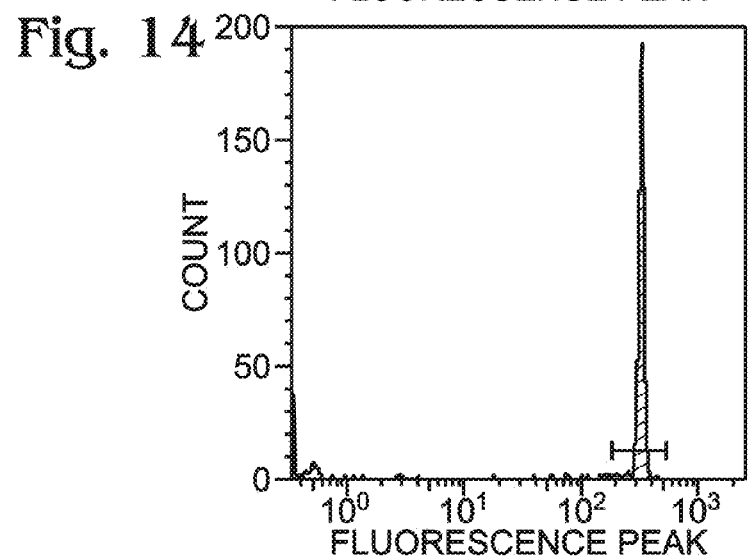

In the analysis of large particle focusing (FIGS. 12-14), the low CV values in each stream imply that our focusing method tightly positioned particles for analysis.[44] The improvement in precision over measurements of smaller particles was expected, as acoustic focusing theory predicts that larger particles experience a greater acoustic force, which results in tighter focusing.[39] Accordingly, the presently described system may be of particular interest for larger particles, as this is one area where traditional flow cytometry has difficulties is the analysis and sorting of particles larger than approximately 70 μm[5] which include analysis of small multicellular organisms, multicellular spheroids, and molecular interactions at the surface of the large microspheres (>100 μm particles) used in 'one-bead one-compound' combinatorial libraries.[43] These difficulties primarily occur due to the increasing likelihood of turbulent flow as the increased particle size conflicts with the high linear velocity required to maintain the high particle analysis rates that are important and/or desirable for most applications.

Figure 15:
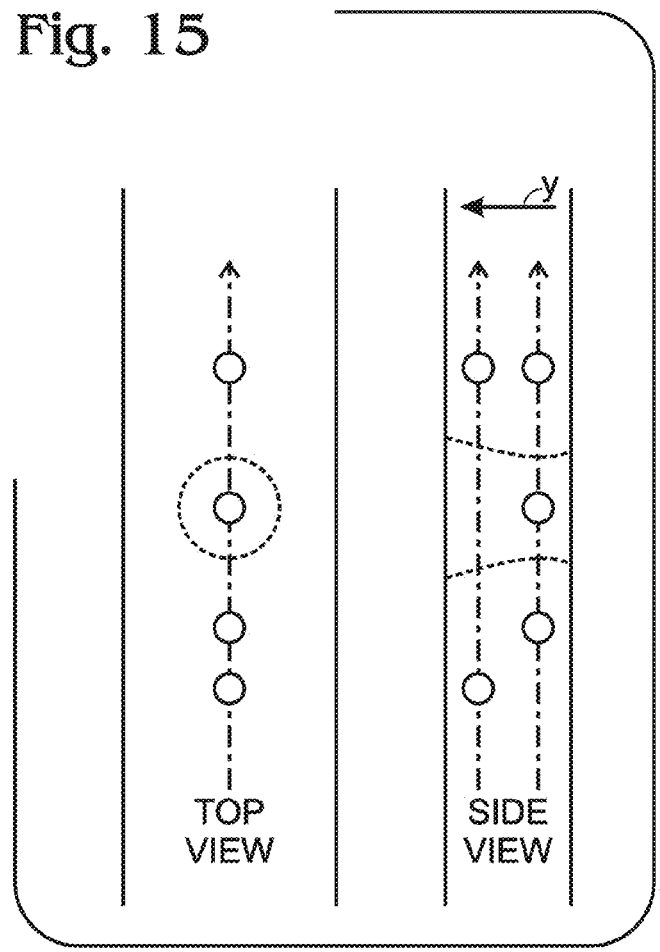
FIG. 15 depicts the random positioning in the vertical plane that can result without additional orthogonal positioning mechanisms.

It will be understood that the acoustic wave field shown in FIG. 1 effectively focuses the particles in the sample stream into multiple parallel streams, which then flow through an analysis region. According to some embodiments, there may be a need for the particles within the streams to be very specifically positioned so as to be accurately measured or otherwise analyzed. For example, in a flow cytometer, it is important that the particles being measured pass directly and precisely through a light beam (which may take the form, for example, of a laser beam, LED light, or other type of light beam) so as to create the optimal interrogation volume for analysis. As shown by comparing the top and side views shown in FIG. 15, without constraint, the particle streams may be displaced relative to each other in the y-direction. According to some embodiments, constraint in the y-direction is provided by the dimensions of the capillary itself—specifically, the walls of the capillary provide sufficient constraint to the particle streams that they are properly positioned in the analysis region.

Figure 16:
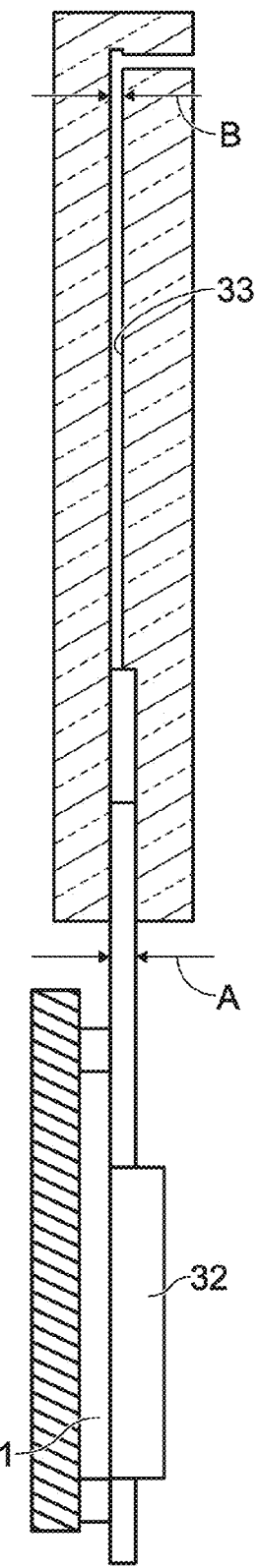
FIG. 16 is a schematic illustration of an exemplary staged multinode acoustic focusing device for single vertical streamline, multiple horizontal streamline analysis according to an embodiment of the present disclosure.

An example of a device that provides physical constraint in the y-direction is shown in FIG. 16. As shown, particles (not shown) are focused to multiple horizontal streamlines in channel 31 by piezoelectric devices 32. The particles then flow into a thinner channel 33 confining them to a single, smaller streamline vertically while maintaining the multiple horizontal streamlines. It will be understood that the channels may be any desired thickness and that the relatively thicknesses of the channel may be determined by a number of factors including, for example, the diameter of the particles to be analyzed in the device. Accordingly, as a specific example, channel 31 may be 100 μm thick dimension A) while channel 33 may be 30 μm thick (dimension B).

Alternatively, a second acoustic wave, directed orthogonally to the first wave, could be applied to further constrain the particles. Of course it is important to note that the acoustic waves described herein are not used to trap the particles to a specific localized position, but rather to separate and precisely position the streams of particles flowing through the capillary.

Figure 17:
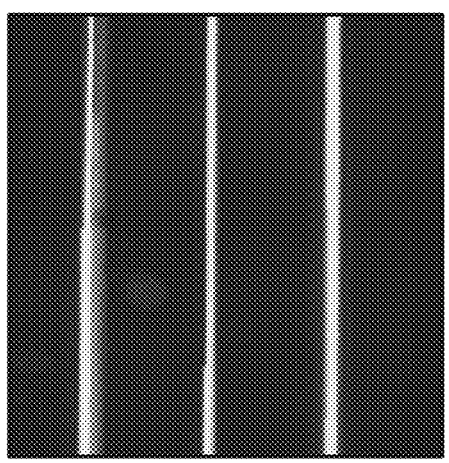
FIG. 17 is a fluorescent micrograph of a focused stream of 10 μm NR-ps particles in a 100×1000 μm glass capillary.
Figure 18:
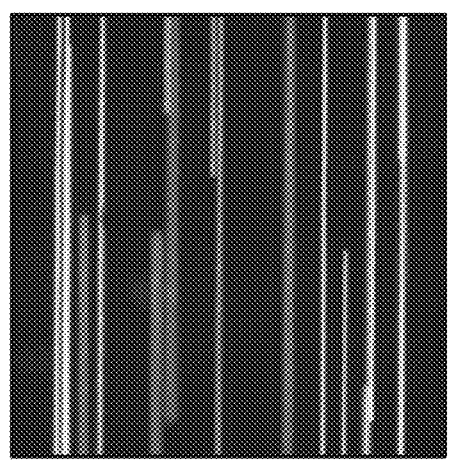
FIG. 18 is a fluorescent micrograph of an unfocused stream of 10 μm NR-ps particles in a 100×1000 μm glass capillary.
Figure 19:
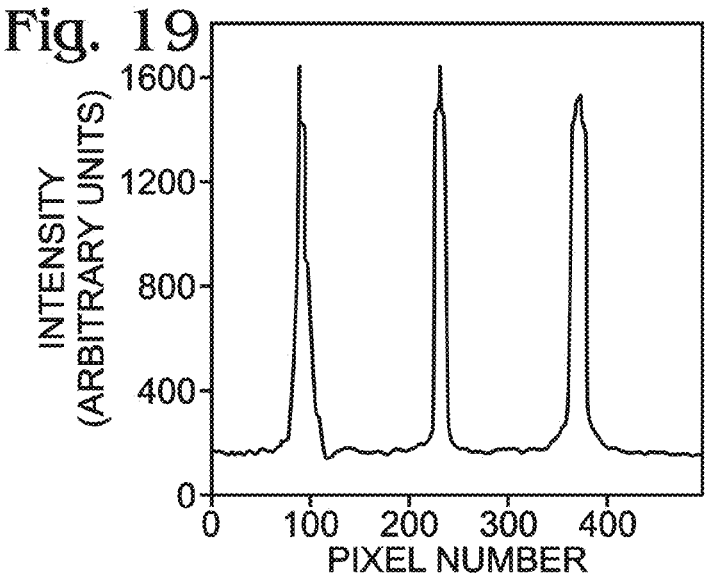
FIG. 19 is fluorescent image analysis of the stream shown in FIG. 17.
Figure 20:
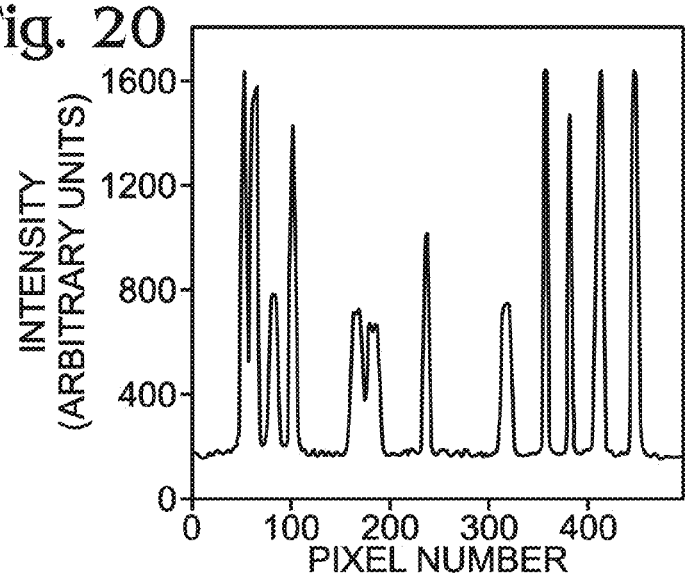
FIG. 20 is fluorescent image analysis of the stream shown in FIG. 18.
Figure 21:
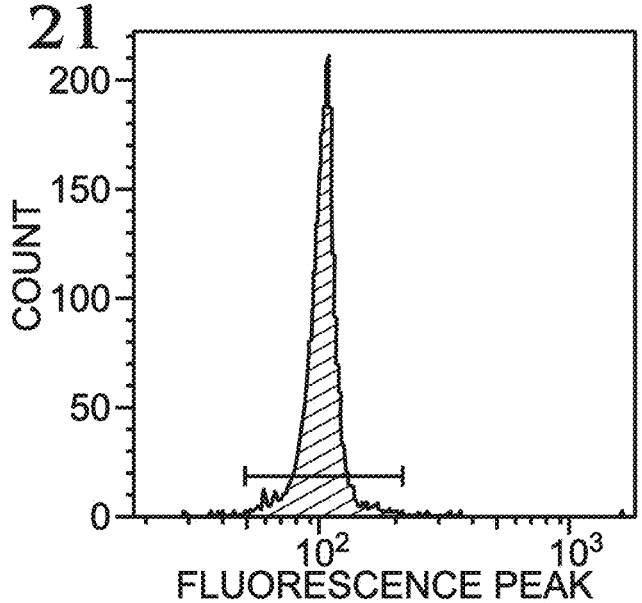
FIG. 21 is flow cytometric analysis of the stream shown in FIG. 17.
Figure 22:
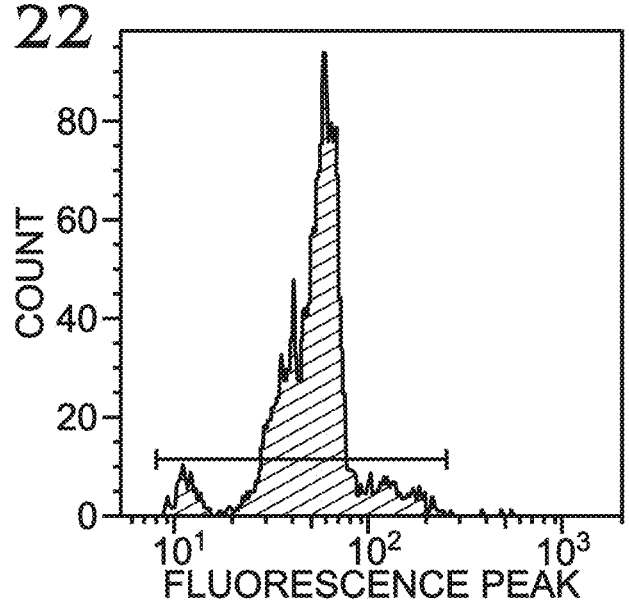
FIG. 22 is flow cytometric analysis of the stream shown in FIG. 18.

The fluorescence images of focused streams shown in FIG. 17 demonstrate that we can obtain highly precise stream focusing 10 μm polystyrene microparticles. (By comparison, FIG. 18 shows a fluorescent micrograph of a non-focused stream including the same particles.) The observed resonance frequency for three stream focusing in glass capillary was 1.49 MHz, but calculation predicts a value of 2.22 MHz, assuming water as the medium. Evander et al. observed similar discrepancies for acoustic focusing in etched glass devices.[42] The outer side walls of these glass capillaries where PZT is attached are not flat. Furthermore, a thin layer of epoxy-glue was used to attach the PZT. Disagreement in calculated and measured resonant frequencies may be due to such structural and material effects. Despite this discrepancy in resonance frequency, three focused streams are placed in equal distance from each other (FIG. 19) and this distance should equal to half wavelength of corresponding resonance frequency. (Again for comparison the fluorescent image analysis of the unfocused stream is shown in FIG. 20) The presence of three distinct peaks found in a time based histogram of intensity (FIG. 21) further suggest that there is no cross talk between focused streams or random transfer of particles between streams once they are focused, which is important as our flow cytometry analysis (see below) is only sensitive to particles that intersect the tightly focused laser. This image analysis demonstrates that no particles are missing the flow interrogation volume during flow cytometry analysis. Again, this analysis can be compared to the flow cytometric analysis of the unfocused stream in FIG. 22.

The quantitative data obtained from custom flow cytometer further indicate the precise particle focusing in these devices. The dramatic reduction of the CV for the focused sample in comparison to un-focused sample (FIGS. 21 and 22) demonstrates that we are achieving effective particle focusing. Potential additional changes to improve focusing could include small amounts of sheath for top-to-bottom focusing, and/or reducing channel height to restrict top-to-bottom position of particles.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a host cell" includes a plurality (for example, a culture or population) of such host cells, and so forth.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

All patents and publications referenced below and/or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

REFERENCES

1. Kiyoyuki Ogata, Yoshifumi Kishikawa, Chikako Satoh et al., *Blood* 108 (3), 1037 (2006).
2. Wai-Ming Lee, Kris Grindle, Tressa Pappas et al., *J. Clin. Microbiol.* 45 (8), 2626 (2007).
3. W. K. W. Li and P. M. Dickie, *Cytometry* 44 (3), 236 (2001).
4. J. Vives-Rego, P. Lebaron, and G. Nebe-von Caron, *FEMS Microbiology Reviews* 24 (4), 429 (2000).
5. H M Shapiro *Practical flow cytometry*. (Wiley Online Library, 2003).
6. I Cruz, *American journal of clinical pathology* 123 (1), 66 (2005).
7. C Criscitiello, C Sotiriou, and M Ignatiadis, *Current Opinion in Oncology* 22 (6), 552 (2010).
8. M C Cheung, J D Goldberg, and Y W Kan, *Nature Genetics* 14 (3), 264 (1996).
9. J O Price, S Elias, S S Wachtel et al., *American journal of obstetrics and gynecology* 165 (6 Pt 1), 1731 (1991).
10. J L Simpson and S Elias, *Jama* 270 (19), 2357 (1993).
11. P Mancuso, A Burlini, G Pruneri et al., *Blood* 97 (11), 3658 (2001).
12. N Werner, S Kosiol, T Schiegl et al., (2005), Vol. 353, pp. 999.
13. C Schmidt-Lucke, L Rossig, S Fichtlscherer et al., *Circulation* 111 (22), 2981 (2005).
14. M. Van Dilla, P. Dean, O. Laerum et al., *Flow cytometry: instrumentation and data analysis*. (Academic Pr, 1985).
15. J C Sharpe and K M Evans, *Theriogenology* 71 (1), 4 (2009).
16. T. Laurell, F. Petersson, and A. Nilsson, *Chemical Society Reviews* 36 (3), 492 (2007).
17. Filip Petersson, Andreas Nilsson, Cecilia Holm et al., *Lab on a Chip* 5 (1), 20 (2005).
18. F. Petersson, A. Nilsson, C. Holm et al., *The Analyst* 129 (10), 938 (2004).
19. John Oakey, Robert W. Applegate, Erik Arellano et al., *Analytical Chemistry* 82 (9), 3862 (2010).
20. P R C Gascoyne and J Vykoukal, *ELECTROPHORESIS* 23 (13), 1973 (2002).
21. P Gascoyne, C Mahidol, M Ruchirawat et al., *Lab on a Chip* 2 (2), 70 (2002).
22. A A S Bhagat, S S Kuntaegowdanahalli, N Kaval et al., *Biomedical microdevices* 12 (2), 187 (2010).
23. S C Hur, H T K Tse, and D D Carlo, *Lab on a Chip* 10 (3), 274 (2010).
24. G Goddard, J C Martin, S W Graves et al., *Cytometry Part A* 69 (2), 66 (2006).
25. G Goddard, J C Martin, M Naivar et al., *Cytometry Part A* 69 (8), 842 (2006).
26. L V King, *Proceedings of the Royal Society of London. Series A, Mathematical and Physical Sciences* 147 (861), 212 (1934).
27. M. Evander, L. Johansson, T. Lilliehorn et al., *Anal. Chem* 79 (7), 2984 (2007).
28. W. T. Coakley, J. J. Hawkes, M. A. Sobanski et al., *Ultrasonics* 38 (1-8), 638 (2000).
29. K. Sritharan, C. J. Strobl, M. F. Schneider et al., *Applied Physics Letters* 88 (5), 054102 (2006).
30. Kenji Yasuda, *Sensors and Actuators B: Chemical* 64 (1-3), 128 (2000).
31. M. Bengtsson and T. Laurell, *Analytical and bioanalytical chemistry* 378 (7), 1716 (2004).
32. P. Augustsson, L. B. Åberg, A. M. K. Swärd-Nilsson et al., *Microchimica Acta* 164 (3), 269 (2009).
33. A. Lenshof, A. Ahmad-Tajudin, K. Ja råas et al., *Analytical chemistry* 81 (15), 6030 (2009).
34. Andreas Nilsson, Filip Petersson, Henrik Jonsson et al., *Lab on a Chip* 4 (2), 131 (2004).
35. Gregory Goddard and Gregory Kaduchak, *The Journal of the Acoustical Society of America* 117 (6), 3440 (2005).
36. Gregory R. Goddard, Claire K. Sanders, John C. Martin et al., *Analytical Chemistry* 79 (22), 8740 (2007).
37. Bjorn Hammarstrom, Mikael Evander, Herve Barbeau et al., *Lab on a Chip* 10 (17), 2251 (2010).
38. M Ward, P Turner, M DeJohn et al., *Current Protocols in Cytometry* (2009).
39. K. Yasuda, S. Umemura, and K. Takeda, *Jpn. J. Appi. Phys. Vol* 34, 2715 (1995).
40. M D Ward, C C Stewart, and G Kaduchak, (Google Patents, 2008).
41. Filip Petersson, Andreas Nilsson, Henrik Jönsson et al., *Analytical Chemistry* 77 (5), 1216 (2005).
42. Mikael Evander, Andreas Lenshof, Thomas Laurell et al., *Analytical Chemistry* 80 (13), 5178 (2008).
43. Jared B. Townsend, Farzana Shaheen, Ruiwu Liu et al., *Journal of Combinatorial Chemistry* 12 (5), 700 (2010).
44. S W Graves, J P Nolan, J H Jett et al., *Cytometry* 47 (2), 127 (2002).
45. John Oakey, Robert W. Applegate Jr., Erik Arellano et al., *Analytical Chemistry* 82, 3862 (2010).

EXAMPLES

Example I

Flow Cell Construction—with Glass Capillaries

Each flow cell was made of a channel, consisting of a glass capillary, with a piezoelectric element on one side to drive the resonance and in some cases one on the opposing side to pick up feedback signals. The piezoelectric element converts electrical pulses into mechanical vibrations and vice versa. Specifically, one of our focusing devices consists of a rectangular fused silica capillary (ID 200 μm by 2000 μm) with a piezoelectric drive element and piezoelectric pickup to monitor the frequency and acoustic coupling of the device (FIG. 5). Two lead zirconate titanate (PZT) ceramic (5 mm×30 mm) with specific resonance frequency are glued to opposing sides of the 2000 µm dimension. The particles (107 µm red fluorescent polystyrene microspheres) at a concentration of $10^7$ particles/mL flowed upward through the device using a syringe pump (Nexus 3000, Chemyx Inc. Stafford, Tex.) while the focusing field was applied through PZT element perpendicular to the direction of flow. The PZT element was operated via a high power RF amplifier (Empower RF Systems, Inglewood, Calif.) and the frequency was set by a waveform generator (33250A, Agilent, Santa Clara, Calif.). In this case we used a frequency tuned near 730 kHz, which resonated in the third harmonic and thus, produced three nodes where the positive contrast particles were clearly focused. Particles were analyzed in flow within this system while particles were focused into all three discreet particle streams (FIG. 5). Sample was analyzed at a volumetric flow rate of 1.6 mL/min.

Example II

Flow Cell Construction—with Machined Metal Frame

Figure 23:
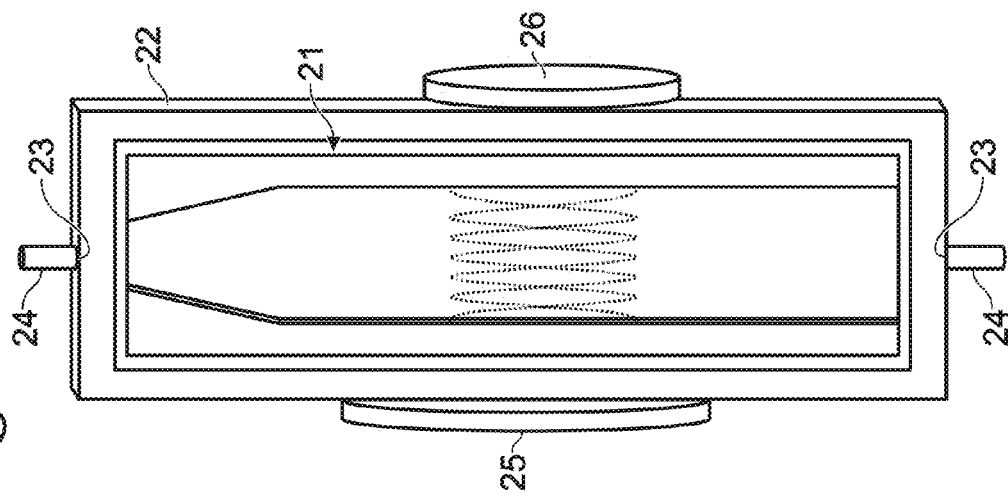
FIG. 23 is a schematic illustration of an exemplary flow cell for flow cytometry machined to produce a high number of parallel streams according to an embodiment of the present disclosure.

As shown in FIG. 23, the flow cell used for generating highly parallel streams of particles was fabricated using two microscope glass slides (25 mm×75 mm) 21 and a micromachined aluminum frame 22. The metal frame had two through holes 23 at the two vertical edges for liquid connection. The frame was sandwiched between the two glass slides and sealed with epoxy glue. Two silicone tubes 24 were attached at the two through-holes as the sample inlet and outlet. A cylindrical piezoelectric transducer 25, (2.5 cm diameter) was ultrasonic gel-coupled to one side of the metal frame and used as the driving element. The acoustic coupling and the strength were monitored via a second cylindrical piezoelectric element 26 (1.25 cm diameter) gel-coupled to the other side of the metal frame. A sample containing 10 µm Nile Red polystyrene particles ($1.36 \times 10^5$ beads/mL) was flowed upward at a flow rate of 250 µL/min using a syringe pump (55-2226, Harvard Apparatus, Holliston, Mass.) (not shown). Once the frequency was fine tuned, particles were focused into highly parallel multiple streams at various resonant frequencies (FIGS. 6-9).

Example III

Imaging

A filter cube set containing 545/25 nm band pass filter for excitation, a beam splitter with fluorescence transmission at 570 nm and 605/70 nm band pass filter for emission was used for image capturing. Image analysis (FIGS. 19 and 20) was performed by line-scanning the image across the capillary.

Example IV

Flow Analysis

Figure 24:
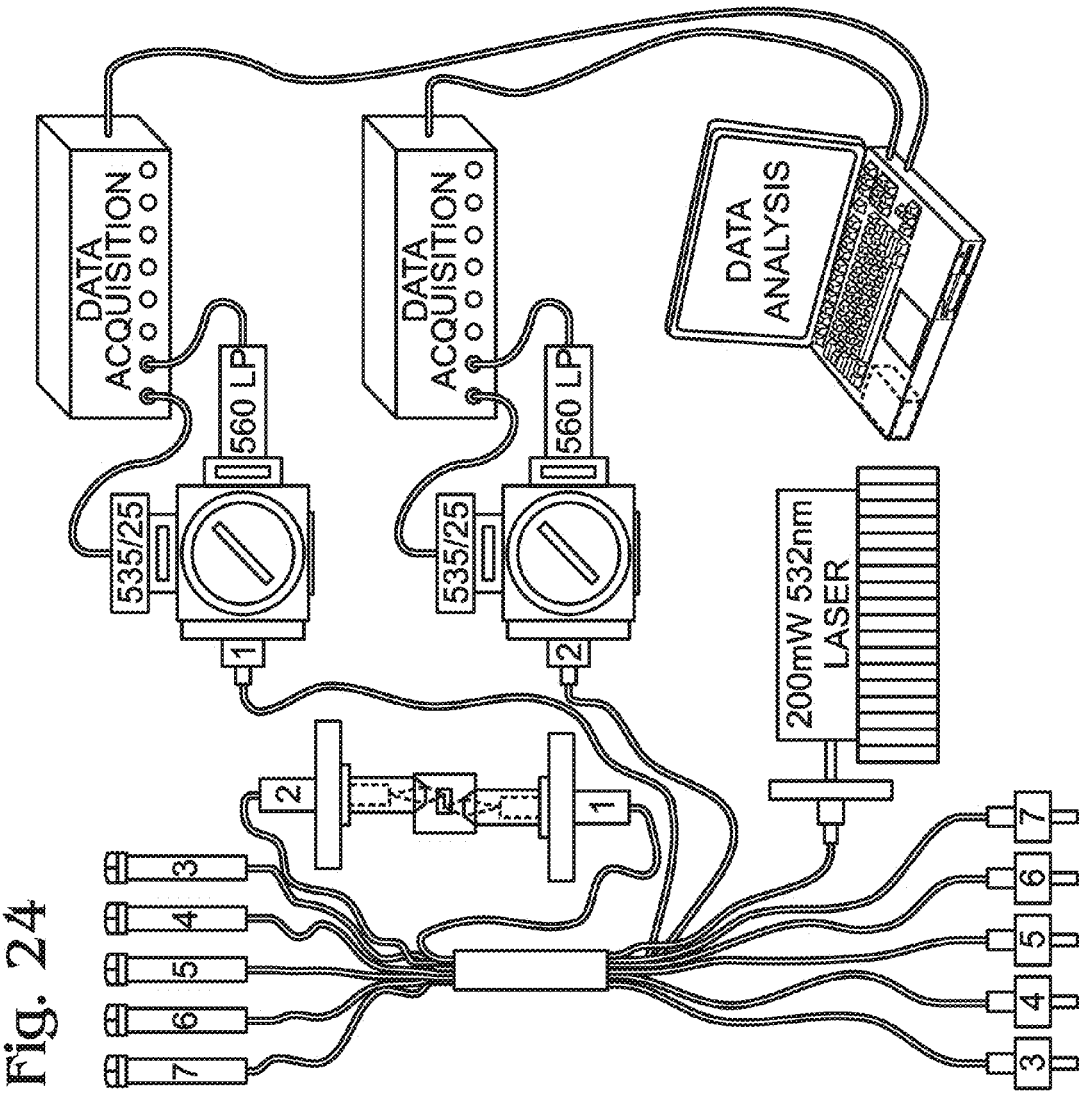
FIG. 24 is Schematic of split fiber analysis system in which a single laser is split to 7 output fibers.

Histograms for each focused stream of 100 µm red fluorescent particles was obtained individually at a flow rate of 1.6 mL/min. To analyze multiple, parallel streamlines simultaneously we designed a custom fiber splitter array as shown in FIG. 24. This fiber system splits a single laser input (200 mW 532 nm) into multiple, equal intensity outputs of approximately 5 mW each. This loss of intensity comes from the fact that most fiber optics were developed for telecommunications and are most efficient in the infrared. Although the intensity is down to 5 mW, this is the same intensity at the sample as the single point analysis system.[45] The laser light exits the fiber at ferrules, which also act to splice in a second fiber for collection. Thus, there is a single emission and detection point of the fiber within the ferrule. The collected light is then sent through the spliced fiber to a designated detector block. Each block contains a 560 nm long pass dichroic that splits the backscatter signal from the collected fluorescence, just as the single analysis system does with conventional optics[45]. A 535/25 nm filter and a 560 nm long pass filter is placed in front of the backscatter photodiode and fluorescence photomultiplier tube respectively. This further reduces noise or wavelength cross talk between the signals. The output/input from the ferrule point in the fiber system passes through a singlet aspheric lens to focus the excitation light and expand the collection light. This combined with the size of the particles (107 µm in this experiment) helps ensure that only a single particle is analyzed within the laser spot at any given time.

What is claimed is:

1. An analytical device comprising:
    a conduit configured to allow a fluid sample to flow through the device in a first direction;
    an acoustic wave generator configured to deliver an acoustic wave across the conduit, such that particles within the conduit are allowed to continue to flow through the conduit in the first direction but are focused by the acoustic wave into at least two distinct particle streams wherein the position of the particles in the particle streams is constrained by the acoustic wave in a second direction and not in the first direction; and
    an analysis region in fluid communication with the conduit, wherein, in the analysis region, the conduit has dimensions that physically constrain the position of the particles in the particle streams in a third direction, but not in the first or second direction, so as to force the particles to be coplanar; such that the combination of the acoustic wave and the conduit dimensions produces multiple coplanar, parallel, single-file, particle streams; and
    a light beam directed at the analysis region;
    wherein a single particle stream passes through the light beam.

2. The analytical device of claim 1 further comprising a plurality of laser beams directed at the analysis region.

3. The analytical device of claim 2 wherein each laser beam interrogates only a single particle stream.

4. The analytical device of claim 1 wherein the particles within the fluid streams are larger than 70 µm.

5. The analytical device of claim 1 wherein the particles within the conduit are focused by the acoustic wave into at least three distinct particle streams.

6. The device of claim 1 wherein the depth of the conduit is less than or equal to 200 µm.

7. The device of claim 1 wherein the depth of the conduit is less than or equal to 100 µm.

8. The device of claim 1 wherein the light beam is tightly focused.

9. The device of claim 1 wherein the channel is rectangular such that it has a cross-sectional aspect ratio wider than it is high.

10. A method for analyzing particles in a fluid sample comprising:
    delivering the fluid sample to a conduit and allowing the fluid sample to flow through an analysis region in the conduit in a first direction;

generating an acoustic wave field across the analysis region, thereby focusing the particles within the fluid sample in a second direction so as to produce at least two distinct particle streams while they flow through the analysis region;

wherein in the analysis region, the conduit has dimensions that cause the particles to be coplanar by restricting the movement of the particles in the particle streams in a third direction but not in the first or second direction; and analyzing the particles in one of the particle streams with a first analytical instrument.

11. The method of claim 10 further comprising selecting a conduit having a constraining dimension that is determined by the size of the particle to be analyzed.

12. The method of claim 10 wherein the combination of the acoustic wave field and channel depth focuses particles flowing through the channel into multiple parallel single file flow streams.

13. The method of claim 10 further comprising analyzing multiple particle streams with multiple analytical instruments, wherein each analytical instrument analyzes only a single particle stream.

14. The method of claim 10 wherein the analytical instruments are tightly focused laser beams.

15. A flow cytometer comprising:

a channel having a channel depth that constricts the particle flow through the channel; and an acoustic wave field extending across the width of the channel;

wherein the combination of the acoustic wave field and channel depth focuses particles flowing through the channel into multiple co-planar parallel single-file flow streams.

16. The flow cytometer of claim 15 further comprising a plurality of individual detectors.

17. The flow cytometer of claim 16 wherein each of the individual detectors is a laser that emits a tightly focused beam of light.

18. The flow cytometer of claim 17 wherein each detector interrogates only a single particle stream.

* * * * *